United States Patent [19]

Mueller et al.

[11] Patent Number: 4,851,580

[45] Date of Patent: * Jul. 25, 1989

[54] PREPARATION OF TRIALKYLAMINES

[75] Inventors: Herbert Mueller, Frankenthal; Roman Fischer, Mutterstadt; Gerhard Jeschek, Gruenstadt; Willibald Schoenleben, Heidelberg, all of Fed. Rep. of Germany

[73] Assignee: BASF Aktiengesellschaft, Ludwigshafen, Fed. Rep. of Germany

[*] Notice: The portion of the term of this patent subsequent to May 2, 2006 has been disclaimed.

[21] Appl. No.: 925,234

[22] Filed: Oct. 31, 1986

[30] Foreign Application Priority Data

Nov. 6, 1985 [DE] Fed. Rep. of Germany ....... 3539266

[51] Int. Cl.$^4$ .............................................. C07C 85/06
[52] U.S. Cl. ..................................................... 564/479
[58] Field of Search ......................................... 564/479

[56] References Cited

U.S. PATENT DOCUMENTS

| 2,609,394 | 9/1952 | Davies et al. | 564/479 |
| 3,128,311 | 4/1964 | Shirley et al. | 564/480 |
| 3,366,687 | 1/1968 | Ellis et al. | 260/583 |
| 3,708,539 | 1/1973 | Fenton | 260/585 B |
| 4,009,124 | 2/1977 | Laurer et al. | 252/463 |
| 4,138,437 | 2/1979 | Strauss et al. | 260/583 R |
| 4,229,374 | 10/1980 | Slaugh et al. | 564/479 |
| 4,234,727 | 11/1980 | Toussaint et al. | 544/178 |
| 4,404,404 | 9/1983 | Swift et al. | 564/473 |
| 4,442,306 | 4/1984 | Mueller et al. | 564/479 |

FOREIGN PATENT DOCUMENTS

| 0024225 | 2/1981 | European Pat. Off. . |
| 1493781 | 6/1965 | Fed. Rep. of Germany . |
| 2445303 | 9/1974 | Fed. Rep. of Germany . |
| 2535073 | 8/1975 | Fed. Rep. of Germany . |
| 2625196 | 6/1976 | Fed. Rep. of Germany . |
| 2838184 | 9/1978 | Fed. Rep. of Germany . |
| 222448 | 3/1984 | Japan . |

Primary Examiner—Richard L. Raymond
Assistant Examiner—Peter G. O'Sullivan
Attorney, Agent, or Firm—Keil & Weinkauf

[57] ABSTRACT

A process for the preparation of tertiary alkylamines having a total of up to 9 carbon atoms by reacting a dialkylamine with a $C_2$-$C_4$-alcohol in the presence of a hydrogenation/dehydrogenation catalyst which contains essentially only copper as the hydrogenating-/dehydrogenating catalytic metal is proposed, wherein the reactants
(a) are present in the liquid phase,
(b) contain alkali metal and/or alkaline earth metal oxides and/or hydroxides and
(c) are reacted in a molar ratio of dimethylamine to alcohol of from 1:10 to 10:1 and
(d) in the presence of the water formed during the reaction.

14 Claims, No Drawings

PREPARATION OF TRIALKYLAMINES

The present invention relates to a process for the preparation of tertiary trialkylamines having a total of up to 9 carbon atoms by reacting a dialkylamine with a $C_2$–$C_4$-alcohol in the presence of a hydrogenation/dehydrogenation catalyst which contains essentially only copper as the hydrogenating/dehydrogenating catalytic metal.

The catalytic alkylation of the amines with alcohols is known. For this reaction, dehydrating oxides, for example those of aluminum, thorium, tungsten and chromium, are used as catalysts on the one hand, while on the other hand hydrogenation and dehydrogenation catalysts based on, for example, copper, nickel, cobalt and chromium have been recommended. Processes in the liquid phase and in the gas phase are known. The field is discussed in detail by V. A. Nekrasova and N. I. Shuikin in Russian Chemical Reviews, 34 (1965), 843 and in the book entitled The Acyclic Aliphatic Tertiary Amines, L. Spialter and J. A. Pappalardo, The Macmillan Company, 1965. It is particularly difficult to prepare tertiary amines by alkylating secondary amines with alcohols. Transalkylation and disproportionation reactions give rise to secondary and primary amines as by-products, and these have an adverse effect on the desired properties of the tertiary amines and are difficult to separate off from the reaction products.

Hence, in order to prepare tertiary amines in high yields, DE-A-1 493 781 describes a process in which not less than the stoichiometric amount of the secondary amine is reacted with the alcohol. Thus, the amine to be reacted should be present in the reaction zone in not less than an equimolar amount, based on the alcohol. It is shown that an excess of alcohol results in poor selectivity with respect to the tertiary amines formed. Although this measure appears to produce a certain improvement in the selectivity with respect to the amine in the reaction of secondary alcohols, the conversion of the amine is low. In the case of primary alcohols, low conversions and poor selectivity are observed in every case because the residues formed as by-products reduce the yield.

An improved process for the preparation of tertiary amines is described in U.S. Pat. No. 3,708,539. In this process, an alcohol is reacted, in the liquid phase, with a secondary amine over a catalyst based on ruthenium, osmium, rhenium or technetium. The disadvantage of this process is the fact that conversion and yield, based on the alcohols used, are unsatisfactory for an industrial process when compared with the value of the catalyst raw materials.

Tertiary amines of the dimethyl-fatty-alklyamine type whose fatty alkyl radical is in general of 8 or more carbon atoms are of particular industrial importance. These products are prepared in large amounts by a wide variety of techniques, either in the gas phase of in the liquid phase.

The synthesis of low molecular weight tertiary trialkylamines presents considerable problems. Examples of prototypes of this class of compounds are dimethylethylamine and triethylamine. These tertiary amines are used industrially on a large scale as catalysts in order to accelerate the polymerization of polyurethane resins, for example in coarse sand binders. Examples of further tertiary amines of this product class are n-propyldimethylamine, methyl ethyl n-propylamine, isopropyldimethylamine and n-butyldimethylamine. All attempts to prepare these low molecular weight tertiary amines by the method which was successful for the synthesis of the long-chain amines have been unsuccessful to date. Hence, DE-A-2 838 184 and EP-B-24 225 have proposed carrying out the synthesis of these compounds over either copper chromite catalysts or pure copper catalysts which are formed by thermal decomposition and reduction of basic copper aluminum carbonates, by reacting, for example, dimethylamine and the low molecular weight alcohol in the gas phase. The use of chromite catalysts is unsuitable from a health point of view, since they are carcinogenic.

Although the synthesis of, for example, dimethylethylamine can be carried out in a technically satisfactory manner by either of the above methods, the synthesis remains unsatisfactory.

Both methods have the disadvantage that, in order to carry out the gasphase reaction, a relatively large amount of energy has to be expended to vaporize the reactants, a relatively large amount of hydrogen and gaseous dimethylamine has to be circulated, and the end product, e.g. dimethylethylamine, can be isolated from the circulated gas only by means of a very expensive condensation procedure. In general, a multistage condensation system comprising a series of condensation units is required. Since these processes are carried out in the gas phase under relatively low hydrogen partial pressures over catalysts which effect not only hydrogenation but also dehydrogenation, the alcohol is also converted to the corresponding aldehyde, which undergoes aldol condensation to give undesirable by-products, which not only reduce the yield but also appear as impurities in the end product. In the synthesis of ethyldimethylamine, the crude reacted mixture contains, for example, acetaldehyde. Hence, the process described in EP-B-24 225 envisages a procedure in which, before the final working up, the initially formed reaction product is fed to a separate hydrogenation stage in which the acetaldehyde is hydrogenated to ethanol in order to avoid difficulties during working up. Although the yields in which the relatively highgrade amines are obtained are very high at more than 90% of theory, they are still unsatisfactory in view of the value of these amines.

A serious disadvantage of the synthesis of dimethylethylamine in the gas phase is that the aldehyde and its condensates are formed as by-products from ethanol, which is a building block of the synthesis. These have to be hydrogenated in a special hydrogenation stage so that they can be removed from the reaction products, or recycled to the reaction as alcohol. Because this additional hydrogenation is difficult, EP-B 24 225 also proposes, as an alternative, removing the aldehydes from the reaction mixture with the aid of hydrazine-hydrate, by forming hydrazones.

The formation of inert substances in the recycle gas of the gas phase process is related to the formation of aldehydes as by-products. The aldehydes tend to decompose as a result of decarbonylation, giving an olefin, hydrogen and carbon monoxide. The inert gases thus formed collect in the recycle gas and have to be separated off continuously. The loss of hydrogen in this process is therefore relatively high.

The formation of the aldehydes in the gas phase process is a possible reason for the relatively short life of the catalysts. The maximum life of a catalyst batch is given as 3 months in EP-B-24 225, page 3, lines 46 and 47.

It is an object of the present invention to provide a process for the preparation of tertiary trialkylamines having a total of up to 9 carbon atoms by reacting a dialkylamine with a $C_2$-$C_4$-alcohol in the presence of a hydrogenation/dehydrogenation catalyst which contains essentially only copper as the hydrogenating-/dehydrogenating catalytic metal, the said process being free of the disadvantages described above. It is intended to provide a process of the stated type which permits the preparation of tertiary trialkylamines, in particular ethyldimethylamine, without a reduction in yield and with the use of only a small amount of thermal and mechanical energy. For this purpose, it is necessary to dispense with the recycle gas procedure otherwise generally recommended, either in the gas phase reaction according to DE-A-2 838 184 and EP-24 225 or in the liquid phase reaction according to the processes described in DE-B-25 35 073 and JP-A 222448/1984.

We have found that this object is achieved by a process of the stated type, wherein the reactants (a) are present in the liquid phase, (b) contain alkali metal and/or alkaline earth metal oxides and/or hydroxides and (c) are reacted in a molar ratio of dialkylamine to alcohol of from 1:10 to 10:1 and (d) in the presence of the water formed during the reaction.

The novel process can be carried out in simple, uncomplicated and therefore cheap apparatuses in virtually quantitative yields. The energy required can be kept small. The catalysts to be used are simple and cheap and have a long life. In the process according to the invention, the formation of undesirable by-products is suppressed and the desired product is obtained with high selectivity. The water formed during the reaction remains in the reaction mixture without having an adverse effect on the yield or rate of the reaction. On the contrary, the yield and the reaction rate increase.

In contrast to the process of EP-B-24 225, during the alkylation of the dialkylamine, aldehydes are not formed at all or are formed in only such a minor amount that they need not be specially removed from the reacted mixture. In contrast to the conventional process, virtually no hydrogen is consumed when a low hydrogen partial pressure is used. There is no need to employ an expensive recycle gas procedure to remove the resulting water from the reaction mixture.

In the novel process, pure copper catalysts are used, either as a fixed bed or in suspension, and the reactants are reacted in the liquid phase in the presence of an alkali metal and/or alkaline earth metal oxide and/ or hydroxide dissolved or suspended in the liquid phase. Suitable alkali metal or alkaline earth metal oxides or hydroxides are the oxides or hydroxides of lithium, of sodium, of potassium, of magnesium, of calcium, of strontium, or of barium, and mixtures of these.

It is also important that the hydrogen partial pressure in the reaction mixture is kept low in comparison with the total pressure.

In contrast to other, previously described processes, according to the invention it is not necessary for the water formed during the reaction to be removed continuously from the reaction mixture in order to achieve complete conversion of the dialkylamine. This latter result, in particular, was not to be expected in the reaction in the liquid phase, since it is known that in other cases (cf. for example DE-C-2 625 196) complete conversion is only achieved if water is removed from the reaction mixture at the rate at which the water is formed. This conforms to the reaction mechanism of the formation of the tertiary amines (hydrolytic cleavage of intermediates formed).

In the novel process, it is possible in particular to react monohydric aliphatic alcohols of 2 to 4 carbon atoms, such as ethanol, n-propanol, isopropanol, nbutanol, sec-butanol or isobutanol, with dialkylamines in the presence or absence of a hydrogen to give the tertiary trialkylamines in virtually quantitative yield. Transalkylation and the formation of secondary or even primary amines are observed only to a small, insignificant extent.

Suitable dialkylamines are secondary amines, such as dipropylamine, ethylmethylamine, diethylamine, dimethylamine or methylbutylamine.

The process can be carried out over a fixed bed catalyst by the liquid-phase or trickle-bed procedure, or over a suspended catalyst.

The procedure over fixed bed catalysts is advantageously carried out as follows. The reactor used is, for example, a vertical cylindrical vessel possessing the usual means of cooling or heating and a means of feeding in the reactants. The reaction vessel is filled with the catalyst, which may be of any shape. Frequently, the catalyst is used in the form of extrudates having a diameter of 3–6 mm and a length of up to 5 cm. However, the catalyst used may also be pelletized in the form of cylinders having, for example, a diameter of 5 mm and a height of 5 mm, or in the form of spheres or in any other form.

If the trickle bed procedure is used, the reactants dialkylamine and alcohol are passed downward through the catalyst-containing reaction vessel, for example at a rate of 200–500 mm of reaction mixture per liter of catalyst per hour, and the desired reaction pressure is established, this pressure being the sum of the vapor pressure of the reactants and reaction products, a low hydrogen partial pressure and any inert gas pressure additionally used. The discharge of waste gas can be substantially dispensed with since virtually no foreign inert gases are formed in the novel process. Consequently, the process is particularly economical in respect of hydrogen consumption. At the end of the furnace, the reaction product is removed continuously from a vessel in which the level is controlled. Since the reaction is slightly exothermic, involving about 7 Kcal/mole, the reaction vessel can be maintained under isothermal conditions by recycling some of the reaction product onto the catalyst bed by means of a circulating pump, after prior cooling. Since the reaction is generally carried out in such a way that either the dialkylamine used or the alcohol is completely converted, the desired tertiary trialkylamine can be obtained in pure form and the reactant used in excess can be employed again for further reactions after being separated off from the water of reaction by distillation.

In addition to this preferred application of the trickle bed procedure described above, the reaction can also be carried out in such a way that the reactants flow through the catalyst bed as a liquid phase, from the bottom upward. In this case too, the heat of reaction can, if required, be removed by recycling. As in the trickle bed procedure, it is also possible to maintain isothermal conditions during the reaction by means of the reactant used in excess.

In the preferred embodiment of the novel process, copper catalysts which are described in DE-A 2 445 303 are used. They may be regarded as amorphous products of the thermal decomposition and reduction of basic copper aluminum carbonates, and are obtained by precipitating dilute or moderately concentrated solutions, advantageously 3M solutions, of copper and aluminum salts with an alkali metal carbonate at pH 8–10, and decomposing the resulting precipitates, before or after appropriate shaping, at 350°–600° C. After reduction in a conventional manner, preferably in the presence of the alcohol used in the subsequent reaction, highly active catalysts which are very suitable for the present process are obtained. However, it is also possible to use copper catalysts which are obtained by impregnating suitable carrier material, e.g. pumice, diatomaceous earth, silica gel, thorium oxide or alumina, and then reducing the product.

In the suspension procedure, which is also possible in the process according to the invention, the reduced copper catalyst is suspended in the reactants, i.e. the alcohol and the dialkylamine. Examples of suitable catalysts are Raney copper or the above copper catalysts in powder form. However, an active copper material obtained by heating copper formate in the presence of an alcohol and a dialkylamine at 200°–250° C. is preferred. The way in which such a catalyst is formed is described in, for example, EP-B-70 512.

The synthesis according to the invention is carried out in the presence of an excess of alcohol or secondary amine. The excess should be no less than a two-fold molar amount, the upper limit being determined only on the basis of economic considerations. Since scarcely any further increase in yield is observed at a molar ratio of amine to alcohol or alcohol to amine of 1:5, the reaction is generally carried out using a molar ratio of amine to alcohol of from 1:5 to 5:1, preferably from 1:4 to 4:1.

A very important novel measure in the present process consists in adding an alkaline earth metal oxide and/or alkali metal oxide or hydroxide to the liquid reactants. This measure makes it possible completely to suppress transalkylation reactions and disproportionation reactions. It is surprising that this effect is not observed when the alkali metal or alkaline earth metal compounds are added to the catalysts themselves, for example in the preparation of the moldings. It is evidently essential for the alkaline earth metal or alkali metal compounds to be available continuously to the reactants over the catalyst. Of course, this statement applies only to the continuous embodiment of the novel process, either over a fixed bed catalyst or, for example, over suspended catalysts in a reaction cascade.

The reaction is carried out at from 160° to 250° C., preferably from 170° to 210° C.

The reaction rate is very high; from 100 to 300 parts by weight of tertiary trialkylamine per liter of catalyst per hour can readily be produced.

In carrying out the novel process, it is found, surprisingly, that the catalysts retain their activity unchanged over extremely long periods. In fixed bed catalysis, for example, the preferred copper catalyst according to DE-A-2 445 303 can be employed for more than 1 year. The same applies to the active copper metal ob-tained as a catalyst from copper formate.

The Examples which follow illustrate the novel process without restricting the invention. Parts are by weight, and parts by weight bear the same relation to parts by volume as that of the kilogram to the liter.

EXAMPLE 1

For the continous preparation of ethyldimethylamine, liquefied technical grade dimethylamine and an ethanol azeotrope (95.6% of ethanol and 4.4% of water) denatured with 1.2% of toluene were used.

The amination was carried out in a vertical reaction tube having a capacity of 1000 parts by volume. The ratio of the diameter to the length of the reaction tube was 1:40. The reaction tube was thermostated by means of an organic heat transfer medium which was circulated in a heating jacket. 700 parts by volume of a catalyst in the form of cylinders having a height of 3 mm and a diameter of 3 mm were introduced into the reaction tube. The catalyst was prepared by the method described in Example 1 of DE-A-2 445 303. It was reduced with hydrogen at 180°–200° C., 300 ml/hour of ethanol being trickled over the catalyst at the same time. The reduction was carried out initially with a hydrogen/nitrogen mixture (50 bar) and subsequently with pure hydrogen, until water of reduction was no longer detectable in the outflowing ethanol azeotrope. 300 parts/hour of ethanol which contained 0.15% of sodium hydroxide and 100 parts/hour of dimethylamine were then fed downward through the oven at 200° C. and under a total pressure of 50 bar (hydrogen partial pressure about 10 bar). About 0.1–0.2 part by volume per hour of hydrogen, as exit gas, was fed to the head of the vessel. Analysis by gas chromatography and by distillation showed that the product leaving the vessel had the following composition:

| trimethylamine | 1% by weight |
| monomethylamine | 1% by weight |
| dimethylamine | 1% by weight |
| dimethylethylamine | 50% by weight |
| diethylmethylamine | 1% by weight |
| ethanol | 32% by weight |
| toluene | 1.5% by weight |

Dimethylethylamine which is more than 99.5% pure can be obtained from this crude mixture by distillation.

A similar result is obtained if, instead of sodium hydroxide, potassium hydroxide or lithium hydroxide is added to the ethanol.

A similar reacted mixture having the composition described above is obtained if, instead of the precipitated catalyst described above, a copper catalyst obtained by impregnation and containing 20% of copper oxide on silica gel is used and about half the feed of the above composition is passed over this catalyst.

EXAMPLE 2

A stirred container having a reaction volume of 2000 parts was charged with 920 parts of ethanol, 180 parts of dimethylamine, 5.5 parts of calcium hydroxide and 55 parts of a metallic copper catalyst.

The copper catalyst had been prepared beforehand from copper formate in a separate reaction at 200° C. in the presence of lauryl alcohol saturated with dimethylamine. Hydrogen under 10 bar was forced into the stirred container at 20° C., after which the contents were heated to 210° C. The total pressure of the reaction system increased to 55–60 bar during this procedure. The system was stirred for 6 hours at the reaction temperature, after which it was allowed to cool, the catalyst was allowed to settle out, and the clear supernatant solution was forced out. It had roughly the following composition:

| | |
|---|---|
| monomethylamine | 0.2% by weight |
| trimethylamine | 0.2% by weight |
| dimethylamine | 0.3% by weight |
| dimethylethylamine | 28% by weight |
| diethylmethylamine | 0.2% by weight |
| unknown substance | 0.7% by weight |
| ethanol | 60% by weight |
| toluene | 1.6% by weight |
| water | 10% by weight |
| high boilers | 0.2% by weight |

Dimethylethylamine having a purity of more than 99.5% was obtained from the reacted mixture by fractional distillation.

EXAMPLE 3

In the reaction apparatus described in Example 2, and using 52 parts of the powdered catalyst described in Example 1 and 2.5 parts of 50% strength sodium hydroxide solution, 925 parts of n-butanol and 103 parts of dimethylamine were reacted with one another under a total pressure of 50 bar (partial pressure of the reaction mixture +hydrogen partial pressure) at 220° C. The mixture was stirred for 10 hours at the reaction temperature, after which it was left to cool, and the reaction product was isolated as described in Example 2. It had the following composition, based on anhydrous product:

| | |
|---|---|
| monomethylamine | 0.1% by weight |
| trimethylamine | 0.9% by weight |
| dimethylamine | 0.1% by weight |
| dimethylbutylamine | 15.9% by weight |
| dibutylmethylamine | 0.3% by weight |
| n-butan-1-ol | 82.7% by weight |

EXAMPLE 4

The procedure described in Example 3 was followed, and 744 parts of diethylamine were reacted with 95 parts of ethanol in the presence of 62 parts of the powdered catalyst described in Example 1 and 2.5 parts of 50% strength sodium hydroxide solution under a total pressure of 50 bar (partial pressure of the reaction mixture +hydrogen partial pressure) and at 210° C. The mixture was stirred for 10 hours at the reaction temperature, after which it was allowed to cool, and the reaction product was isolated as described. It had the following composition, determined by gas chromatography and based on

| anhydrous product | |
|---|---|
| unknown substance | 0.3% by area |
| monoethylamine | 3.1% by area |

-continued

| | |
|---|---|
| diethylamine | 47.9% by area |
| triethylamine | 47.6% by area |
| ethanol | 1.1% by area |

We claim:
1. A process for the preparation of a trialkylamine having a total of up to 9 carbon atoms which comprises: reacting a dialkylamine with a $C_2$–$C_4$-alcohol in the presence of a hydrogenation/dehydrogenation catalyst which contains essentially only copper as the hydrogenating/dehydrogenating catalytic metal, wherein
   (a) the reactants are present in the liquid phase,
   (b) an alkali metal and/or alkaline earth metal oxide and/or hydroxide is dissolved in the liquid,
   (c) the reactants are present in a molar ratio of dialkylamine to alcohol of from 1:10 to 10:1 and
   (d) the reaction takes place in the presence of the water formed during the reaction.
2. The process as claimed in claim 1, wherein the molar ratio of dialkylamine to alcohol in the reaction is from 1:4 to 4:1.
3. The process as claimed in claim 1, wherein the reaction is carried out at from 160° to 250° C.
4. The process as claimed in claim 1, which is carried out in the presence of hydrogen.
5. The process as claimed in claim 1, wherein no recycled gas and less than 1 l of exit gas per liter of catalyst per hour is circulated.
6. The process as claimed in claim 1, wherein the reaction is carried out under a total pressure of from 40 to 250 bar and under a hydrogen partial pressure of from 2 to 30 bar.
7. The process as claimed in claim 1, wherein a fixed bed copper catalyst is used.
8. The process as claimed in claim 1, wherein the catalyst used is obtainable by thermodecomposition and reduction of a basic copper aluminum carbonate, the latter being formed by precipitating a solution containing copper and aluminum salts at pH 8–10.
9. The process as claimed in claim 1, which is carried out in the presence of a suspended copper catalyst.
10. The process as claimed in claim 1, wherein the copper catalyst used is obtainable by heating copper formate in the presence of an alcohol and dialkylamine at above 170° C.
11. The process of claim 1, wherein the alkali metal or alkaline earth metal oxide and/or hydroxide is continuously added to the reaction liquid along with the reactants.
12. The process of claim 1, wherein the alkali metal or alkaline earth metal oxide or hydroxide is sodium hydroxide.
13. The process of claim 11, wherein the dialkylamine is dipropylamine, ethylmethylamine, diethylamine, dimethylamine or methylbutylamine.
14. The process of claim 11, wherein the dialkylamine is dimethylamine and the alcohol is ethanol.

* * * * *